US010533012B2

(12) United States Patent
Pardal Filipe et al.

(10) Patent No.: US 10,533,012 B2
(45) Date of Patent: *Jan. 14, 2020

(54) (R)-PIRLINDOLE AND ITS PHARMACEUTICALLY ACCEPTABLE SALTS FOR USE IN MEDICINE

(71) Applicant: TECNIMEDE SOCIEDADE TECNICO-MEDICINAL S.A., Sintra (PT)

(72) Inventors: Augusto Eugénio Pardal Filipe, Lisbon (PT); Pedro Filipe Eufrásio Pedroso, Lisbon (PT); Susana Marques Almeida Pecorelli, Alcabideche (PT); Carlos Alberto Eufrásio Casimiro Caixado, Mafra (PT); Ana Sofia da Conceição Lopes, Milharado (PT); João Carlos Ramos Damil, Torres Vedras (PT)

(73) Assignee: TECNIMEDE SOCIEDADE TECNICO-MEDICINAL S.A., Sintra (PT)

( * ) Notice: Subject to any disclaimer, the term of this patent is extended or adjusted under 35 U.S.C. 154(b) by 0 days.

This patent is subject to a terminal disclaimer.

(21) Appl. No.: 15/846,440

(22) Filed: Dec. 19, 2017

(65) Prior Publication Data

US 2018/0111944 A1    Apr. 26, 2018

Related U.S. Application Data

(63) Continuation of application No. 15/309,916, filed as application No. PCT/PT2014/000028 on May 9, 2014.

(51) Int. Cl.
| | |
|---|---|
| A61K 31/4985 | (2006.01) |
| C07D 487/04 | (2006.01) |
| A61P 25/04 | (2006.01) |
| A61K 45/06 | (2006.01) |
| A61K 9/20 | (2006.01) |

(52) U.S. Cl.
CPC .......... *C07D 487/04* (2013.01); *A61K 9/2018* (2013.01); *A61K 9/2054* (2013.01); *A61K 9/2095* (2013.01); *A61K 31/4985* (2013.01); *A61K 45/06* (2013.01); *C07B 2200/07* (2013.01)

(58) Field of Classification Search
CPC .............. C07D 487/04; A61K 31/4985; A61K 9/2018; A61K 9/2054; A61K 9/2095
See application file for complete search history.

(56) References Cited

U.S. PATENT DOCUMENTS

| | | | |
|---|---|---|---|
| 9,814,712 B2 * | 11/2017 | Pardal Filipe | ......... A61K 45/06 |
| 2004/0106681 A1 | 6/2004 | Rao et al. | |
| 2017/0143709 A1 | 5/2017 | Pardal Filipe et al. | |
| 2017/0143710 A1 | 5/2017 | Pardal Filipe et al. | |

FOREIGN PATENT DOCUMENTS

WO    2015171004 A1    11/2015

OTHER PUBLICATIONS

Definition of prevent, Princeton University "About WordNet." WordNet. Princeton University. 2010. <http://wordnet.princeton.edu>, accessed Sep. 18, 2012.*
Foulkes et al. PLOS Genetics 2008, 4 (7), e1000086, p. 1-9.*
Branco et al. Clin. Drug Investig. 2011, 31 (10), 675-689.*
Amelin,et al., "The combined use of acupuncture and antidepressants for managing the spondylogenic lumbosacral pain syndrome", Farmakologiya I Toksikologiya, vol. 54, No. 5, 1991, 1 page, XP055130728.
Andreeva, et al., "Antidepressant-Enhanced Analgesic Action of Clonidine", Pharmaceutical Chemistry Journal, vol. 31, No. 4, Apr. 1, 1997, pp. 166-167 (2 pages), XP055130715.
Häuser,et al., "Treatment of Fibromyalgia Syndrome with Antidepressants: A Meta-analysis", JAMA, vol. 301, No. 2, Jan. 14, 2009, pp. 198-209 (12 pages), XP055130756.
International Search Report and Written Opinion dated Jul. 31, 2014, from the International Bureau in counterpart International application No. PCT/PT2014/000028.
Repta, et al., "Utilization of an Enantiomer as a Solution to a Pharmaceutical Problem: Application to Solubilization of 1,2-Di(4-piperazine-2,6-dione)propane", Journal of Pharmaceutical Sciences, vol. 65, No. 2, Feb. 2, 1976, pp. 238-242 (5 pages), XP055130861.
Tullio, et al., "Effective Resolution of Racemic Pirlindole at the Preparative Scale", Chirality, vol. 11, No. 4, Mar. 29, 1999, pp. 261-266 (6 pages), XP055131009.

* cited by examiner

*Primary Examiner* — Irina Neagu
(74) *Attorney, Agent, or Firm* — Sughrue Mion, PLLC

(57) ABSTRACT

(R)-pirlindole or its pharmaceutically acceptable salts, as well as pharmaceutical compositions comprising the same for use in the therapeutic treatment and prevention of pain.

17 Claims, No Drawings

(R)-PIRLINDOLE AND ITS PHARMACEUTICALLY ACCEPTABLE SALTS FOR USE IN MEDICINE

CROSS REFERENCE TO RELATED APPLICATIONS

This application is a Continuation Application of U.S. application Ser. No. 15/309,916 filed Nov. 9, 2016, which is a National Stage of International Application No. PCT/PT2014/000028 filed May 9, 2014, the contents of all of which are incorporated herein by reference in their entirety.

FIELD OF THE INVENTION

The present invention relates to (R)-pirlindole enantiomer or its pharmaceutically acceptable salts, as well as compositions comprising the same for use in the therapeutic treatment and prevention of pain.

PRIOR ART BACKGROUND

The treatment of pain conditions is of utmost importance in medicine, leading to a worldwide need for additional therapies for its treatment and prevention.

Pain is the most common symptom for which patients seek medical attention. Although there is no exact definition it can be defined as an unpleasant sensory and emotional experience associated with actual or potential tissue damage, or described in terms of such damage (International Association for the Study of Pain, IASP).

Pain is a very relevant symptom that presents a complex pathogenesis. Its presence is described in a large number of syndromes and diseases in medicine. In severe forms, pain translates into disabilities of diverse nature, difficulty in performing daily activities, interference with mood, professional performance and social relations.

Furthermore, the interpretation of pain varies from individual to individual, and within the individual himself, at different times of his life, depending on varying physical, biological, socio-cultural and emotional conditions.

Regarding the topographic distribution it is possible to distinguish three types of pain: peripheral pain, central pain and psychogenic pain.

Peripheral pain is the result of an organic disorder in peripheral nerve fibers, which, while transmitting nerve impulses, originate the sensation of pain. Peripheral pain further divides into superficial Peripheral pain and deep peripheral pain. The first is acute and penetrating and it is located at the point of origin. Deep peripheral pain may be classified as somatic or visceral. Somatic deep peripheral pain can be localised (pain is located at the point of origin of the painful stimulus) or radiating (pain is diffuse and distant from the point of origin of the painful stimulus). Finally, deep visceral peripheral pain has a difficult topography to limit.

Central pain is a spontaneous pain resulting from neurological injury of central nerve centres such as the spinal cord, medulla oblongata, the thalamus or the cerebral cortex.

Psychogenic pain is defined as a painful sensation that does not have an organic substrate. It is any pain that is exclusively mental, which acquires a specific anatomical location.

From the pathophysiological point of view, pain can be nociceptive or neuropathic.

Nociceptive pain can be defined as pain that arises from actual or threatened damage to non-neural tissue and is due to the activation of nociceptors. Nociceptive pain can be classified as somatic or visceral. Somatic pain is due to activation of the nociceptive receptors in somatic tissues, such as bone, joint, muscle or skin. In visceral pain the visceral nociceptors are activated by different pathological mechanisms (e.g. mechanical injury, inflammation, radiation, toxic agents). Both visceral and somatic nociceptive pain can be acute or chronic. Visceral pain is more difficult to characterise and less sensitive to usual pain treatment. Some pain syndromes (e.g., cancer pain) include elements of both visceral and somatic nociceptive pain.

Neuropathic pain can be defined as pain arising as a direct consequence of a lesion or disease affecting the somatosensory system (i.e. peripheral nerve, the dorsal root ganglion or dorsal root or the central nervous system).

Almost any of the pathological processes known to create damage or dysfunction to neural tissue can be considered as potential causes for neuropathic pain: viral, bacterial, aseptic inflammation, pressure due to neoplasm or other structural lesions, degenerative, ischemia, autoimmune, toxic, traumatic or endocrine/metabolic mechanisms all have been implicated in the production of neuropathic pain.

However, the most commonly studied neuropathic pain conditions include diabetic neuropathic pain (diabetic NP), post-herpetic neuralgia (PHN), trigeminal neuralgia and central neuropathic pain (spinal cord injury (SCI), central post-stroke pain (CPSP) and multiple sclerosis associated pain).

Other neuropathic pain conditions include neuropathy associated with HIV infection (HIV neurepathy), post-traumatic or post-surgical neuropathio pain, chronic radiculopsthy, cancer associated neuropathic pain, phantom pain and multi-aetiology neuronathic pain.

Neuropathy is a functional disorder or pathological change that affects the nerves. It is called mononeuropathy if involves a single nerve trunk, multiple mononeuropathy if it successively involves several nerve trunks and polyneuropathy if involves, diffusely and bilaterally, several nerve trunks.

Peripheral neuropathies may be sensory, motor or autonomic. The most frequent motor manifestations are muscle spasms, clonus, fasciculations, amyotrophy and the loss of muscle strength or dexterity.

Negative sensory manifestations include hypoalgesia and hypoesthesia. In turn, positive sensory manifestations include paresthesia, dysesthesia, hyperpathia, hyperalgesia and allodvnia, aside from the sensation of pricking, tingling or tinnitus. Examples of neuropathy include, peripheral polyneuropathy, characterised by a burning or needle pricking sensation in the feet and fingertips, which is worsened by walking, allodynia, feet hypoesthesia, and absence of Achilles reflex; trigeminal neuralgia, characterised by severe acute pain, shock-like, with duration of seconds in the upper lip and nose, which worsens with chewing or brushing and which is not accompanied by changes in the neurological examination; carpal tunnel syndrome, characterised by acute pain, tingling sensations and reduced sensitivity in the $1^{st}$, $2^{nd}$ and $3^{rd}$ fingers and palmer surface of the hand, that worsens at night, with decreased muscle strength in thumb abduction and positive Phalen test; mononeuropathy of the lateral cutaneous nerve of the thigh, characterised by a burning and pricking sensation to the side of the thigh and presence of a circumscribed area of cutaneous hypersensitivity; postherpetic neuralgia, characterised by a burning pain with banner-like distribution on the thoracic region after the appearance of vesicles, which does not improve after skin healing, hyperchromic skin spots and allodynia.

The impact of pain on individual and social welfare has increased in recent decades.

To this regard, neuropathic pain is widely recognised as one of the most difficult pain syndromes to manage, and outcomes often are unsatisfactory. Neuropathic pain is estimated to afflict as high as 7-8% of the general population in Europe (European Federation of Neurological Societies guidelines on the pharmacological treatment of neuropathic pain, 2010).

Management of neuropathic pain is a complicated endeavour and often is frustrating to patient and physician alike. Drugs with mechanisms of action that are not aimed at changing the underlying physiopathological processes, or that are administered at sub-therapeutic doses, are frequently used in the treatment of pain, and a fortiori of neuropathic pain.

This stems from the relatively incomplete understanding of the mechanism of action of drugs and the limited efficacy of currently available analgesics. Therapeutic approaches vary greatly among physicians and recalcitrant chronic pain syndromes warrant an interdisciplinary approach and more potent pharmacotherapies.

The use of analgesic medications follows a step-wise approach. The $1^{st}$ step corresponds to mild pain, and should be treated with non-opioid analgesic drugs (anti-inflammatory drugs and paracetamol); the $2^{nd}$ is moderate pain, for which weak opioids are indicated and, in the third step, for severe pain, strong opioids are indicated. Depending on the intensity of pain, therapy should be initiated at the corresponding level, with appropriate doses. If the pain persist or worsens, drug doses should be optimised.

Analgesic drugs can be distributed in two large groups non-opioid and opioid analgesic drugs.

Non-opioid analgesic drugs include paracetamol and non-steroidal anti-inflammatory drugs (NSAIDs). Paracetamol does not have a well known mechanism of action although a central action is assumed. The administration of large doses either acutely or chronically, involves a risk of hepatotoxicity associated with depletion of sulfhydryl radicals.

Nonsteroidal anti-inflammatory drugs act by inhibiting cyolooxygenase (COX), inhibiting the synthesis of prostaglandins (PG) involved in the inflammatory process and in pain. They may be non-selective, inhibiting COX and $COX_2$, as acetylsalicylic acid (AAS), ibuprofen or diclofenac, or selective, inhibiting only $COX_2$, as celecoxib, rofecoxib or etoricoxib. Nonsteroidal anti-inflammatory drugs present several side effects, including gastrointestinal (nausea, epigastralgia, ulceration, bleeding), renal (acute renal failure, interstitial nephritis), haematological (platelet anti-aggregation, haemorrhage) or hypersensitivity reactions. These effects are most notorious with non-selective NSAIDs. The main side effect with $COX_2$ inhibitors is an increased cardiovascular risk, by inhibiting prostacyclin. Nonsteroidal anti-inflammatory drugs treatment is associated with an increased risk of gastrointestinal adverse reactions.

The so-called weak opioid drugs include drugs like tramadol, hydrocodone and dextropropoxyphene. These drugs have a maximum posology due to the increased incidence of adverse reactions at high doses. Tramadol is a synthetic derivative of codeine that acts by binding to opioid p receptors and inhibiting neuronal reuptake of serotonin. Tramadol is metabolised in the liver and undergoes renal elimination, therefore it may require dose decrease or prolonged interval between doses in patients with kidney or renal failure.

Hydrocodone is a synthetic derivative of codeine and dextropropoxyphene and presents a structure similar to methadone. Patients with mild to moderate pain should be treated with a weak opioid associated with a NSAID or paracetamol. If pain cannot be controlled at therapeutic doses, a switch to another drug in this group should not be considered and more potent opioids should be used.

Opioids act by binding to receptors $\mu$, $\kappa$, and $\delta$ and may be classified, according to their intrinsic activity, in agonists (morphine, fentanyl, methadone, oxycodone, hydromorphone and pethidine), partial agonist/antagonist (buprenorphine) and agonist/antagonist (pentazocine). A pure agonist is a drug which exerts effect on $\mu$ receptors and on the other receptors. A partial agonist/antagonist exerts a partial agonist effect on a receptor and antagonist effect in at least one receptor, and an agonist/antagonist exerts a pure agonist effect on a receptor and an antagonist effect on at least one receptor.

Opioids induce predictable undesirable side effects, which if not minimised can hamper dose titration and the patient's treatment compliance. Side effects include respiratory depression, nausea and vomiting, constipation, urinary retention, euphoria, sedation, miosis, antitussive action, hypotension, bradycardia, cognitive changes (hallucinations, delusional ideas), hyperalgesia, myoclonus, dyspepsia, pruritus, tolerance and dependence.

Morphine can be administered by oral or parenteral route (subcutaneous and intravenous). Intravenous administration requires specific care and its use is limited to the inpatient setting. For subcutaneous administration infusion pumps are used.

Tricyclic antidepressants (amitriptyline, nortriptyline and desipramine) are used in combination with analgesic drugs, particularly in combination with opioids and mostly in the treatment of neuropathic pain. Due to their anticholinergic action, adverse reactions include constipation, xerostomia, urinary retention and tachycardia.

Anticonvulsants (carbamazepine, oxcarbazepine, phenytoin, sodium valproate, clonazepam, lamotrigine, gabapentin, pregabalin) are also used in the treatment of pain, especially neuropathic pain. Carbamazepine and phenytoin can cause liver toxicity, leukopaenia and thrombocytopaenia, thus requiring monitoring of serum concentrations.

Corticosteroids, of which dexamethasone is most often used for the treatment of pain, are associated with the onset of gastrointestinal disorders, diabetes mellitus, neuro-psychiatric disorders and proximal myopathy.

Therefore it is still a need in the state of the art to find new therapeutic approaches for the treatment of pain, not only as a symptom of disease, but as a disease itself.

The problem that the present invention solves is the provision of an alternative, new and effective agent for the treatment of pain, which alone or in combination with other analgesic agents provides an effective treatment of pain with reduced side effects while maintaining the desirable analgesic activity.

BRIEF DESCRIPTION OF THE INVENTION

The present invention is based on the findings that the optically active compound (R)-pirlindole enantiomer shows an advantageous analgesic activity, useful for the therapeutic treatment and prevention of pain.

The inventors of the present invention have surprisingly found that the optically active (R)-pirlindole enantiomer shows an antagonistic effect on $\alpha_{2A}$ adrenergic receptors, which in turn explains the unexpected activity of (R)- pirlindole enantiomer, in the therapeutic treatment and prevention of pain, in particular, neuropathic pain.

(R)-pirlindole is shown to be an effective agent for the treatment and prevention of pain, in particular, neuropathic pain, when used alone as the sole active ingredient or in a combination therapy with additional analgesic agents, where (R)-pirlindole has been proven to also potentiate the effect of these additional analgesic agents.

The object of the present invention is therefore directed no the provision of (R)-pirlindole or a pharmaceutically acceptable salt thereof as an analgesic agent, for the treatment of pain.

A further object of the present invention is also directed to the provision of (R)-pirlindole or a pharmaceutically acceptable salt thereof alone or as part of a combination therapy with at least one additional analgesic agent, for the treatment of pain.

An additional object of the present invention is also directed to the provision of a pharmaceutical composition comprising (R)-pirlindole or a pharmaceutically acceptable salt thereof together with acceptable carriers, vehicles and/or suitable excipients, for the treatment of pain.

A further object of the present invention is also directed to the provision of a pharmaceutical composition comprising (R)-pirlindole or a pharmaceutically acceptable salt thereof, in combination with at least one additional analgesic agent and together with acceptable carriers, vehicles and/or suitable excipients, for the treatment of pain, where both of (R)-pirlindole or a pharmaceutically acceptable salt thereof and the other analgesic agents are formulated so as to be administered in a fixed-dose or separate dose, such for simultaneous or sequential administration.

A still further object of the present invention is also directed to (R)-pirlindole or a pharmaceutically acceptable salt thereof, for use in a combination therapy with additional analgesic agents, for potentiating the effects of these additional analgesic agents in the treatment of pain.

The present invention further provides a method for the treatment of pain in a subject in need thereof, characterized by administering to the subject an effective amount of (R)-pirlindole or a pharmaceutically acceptable salt thereof, alone or in combination with at least one additional analgesic agent.

The present invention further provides a method for the treatment of pain in a subject in need thereof, by potentiating the effect of the additional analgesic agents, characterized by administering to the subject an effective amount of (R)-pirlindole or a pharmaceutically acceptable salt thereof in combination with additional analgesic agents.

DETAILED DESCRIPTION OF THE INVENTION

In the context of the present invention, the following terms have the meaning described below:

"Pain" as used in the present invention encompasses any unpleasant sensory and emotional experience associated with actual or potential damage, or described in terms of such damage. It includes: peripheral pain, central pain and psychogenic pain, and comprises superficial peripheral pain, deep peripheral pain, somatic deep peripheral pain, visceral deep peripheral pain, pain resulting from neurological injury of central nerve centres such as the spinal cord, medulla oblongata, the thalamus or the cerebral cortex, and psychogenic pain that does not have an organic substrate.

Further, "pain" comprises nociceptive or neuropathic pain. Nociceptive pain arises from actual or threatened damage to non-neural tissue and which is duo to the activation of nociceptors, and being classified as somatic or visceral. Somatic pain is due to activation of the nociceptive receptors in somatic tissues (e.g. bone, joint, muscle or skin). In visceral pain the visceral nociceptors are activated by different pathological mechanisms (e.g. mechanical injury, inflammation, radiation, toxic agents). Both visceral and somatic nociceptive pain can be acute or chronic, and include, cancer pain.

"Neuropathic pain" according to the present invention can be defined as pain arising as a direct consequence of a lesion or disease affecting the somatosensory system (i.e. peripheral nerve, the dorsal root ganglion or dorsal root, or the central nervous system) and includes pain associated to:

Neuropathies, which are a functional disorder or pathological change that affects the nerves, such as mononeuropathy if it involves a single nerve trunk, multiple mononeuropathy if it successively involves several nerve trunks and polyneuropathy if it involves, diffusely and bilaterally, several nerve trunks.

Peripheral neuropathies which may be sensory, motor or autonomic. The most frequent motor manifestations include muscle spasms, clonus, fasciculations, amyotrophy and the loss of muscle strength or dexterity.

Negative sensory manifestations such as, hypoalgesia and hypoesthesia.

Positive sensory manifestations, such as, paresthesia, dysesthesia, hyperpathia, hyperalgesia and allodynia, aside from the sensation of pricking, tingling or tinnitus.

Among others, examples of neuropathic pain include: diabetic neuropathic pain (diabetic NP), post-herpetic neuralgia (PHN), trigeminal neuralgia and central neuropathic pain (spinal cord injury (SCI), central post-stroke pain (CPSP) and multiple sclerosis associated pain, neuropathy associated with HIV infection (HIV neuropathy), post-traumatic or post-surgical neuropathic pain, chronic radiculopathy, cancer associated neuropathic pain, phantom pain and multi-aetiology neuropathic pain, peripheral polyneuropathy, characterised by a burning or needle pricking sensation in the feet and fingertips, which is worsened by walking, allodynia, feet hypoesthesia, and absence of Achilles reflex; trigeminal neuralgia, characterised severe acute pain, toxic neuropathies, compression neuropathies and trauma, which are characterized by spontaneous lancinating, burning pain and shock-like pain as well as pain hypersensitivity including tactile allodynia, pin prick hyperalgesia and hyperpathia, shock-like pain with duration of seconds in the upper lip and nose, which worsens with chewing or brushing and which is not accompanied by changes in the neurological examination; carpal tunnel syndrome, characterised by acute pain, tingling sensations and reduced sensitivity in the $1^{st}$, $2^{nd}$ and $3^{rd}$ fingers and primary surface of the hand, that worsens at night, with decreased muscle strength in thumb abduction and positive Phalen test; mononeuropathy of the lateral cutaneous nerve of the thigh, characterised by a burning and pricking sensation to the side of the thigh and presence of a circumscribed area of cutaneous hypersensitivity; postherpetic neuralgia, characterised by a burning pain with banner-like distribution on the thoracic region after the appearance of vesicles, which does not improve after skin healing and hyperchromic skin spots.

The term "potentiation of the effect of additional analgesic agents", means that the coadministration, in a fixed-dose or separate dose, such as, in simultaneous or sequential form of (R)-pirlindole and at least one additional analgesic agent, including opioids and opiates, enhances the analgesic effect of the latter, allowing for a lower dose of active agents to be administered and reducing the risk of occurrence of adverse reactions, dependence and tolerance.

For purposes of this invention, it is considered as enantiomerically pure when enantiomeric purity as calculated by chiral chromatography or specific optical rotation is equal to or greater than 97%.

The term "pharmaceutically acceptable salt" refers to those salts that are within the scope of proper medicinal assessment, suitable for use in contact with human tissues and organs and those of lower animals, without undue toxicity, irritation, allergic response or similar and are consistent with a reasonable benefit/risk ratio. Pharmaceutically acceptable salts are technically well known. A list of preferred salts, in the context of the present invention, is mentioned in this description.

The term "pharmaceutically acceptable carrier" as used here, means a solid, semi-solid or inert fluid excipient, filler, encapsulating or formulation aiding material of any kind already known by one skilled in the art.

Pirlindole, 2,3,3a,4,5,6-hexahydro-8 methyl-1H-pyrazino [3, 2, 1-j, k] carbazole, is a tetracyclic compound of the following formula:

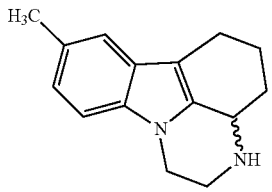 [SMILES: Cc1ccc2c(c1)c1c3n2CCNC3CCC1]

Pirlindole is a reversible inhibitor of monoamine oxidase A (MAO-A) so far useful as a medicine in the treatment of depression.

Pirlindole has an asymmetric carbon atom, but to date only the racemate, (rac)-pirlindole, corresponding to a mixture of both enantiomers (R) and (S) in equal amounts, is used in medicine.

(R)-pirlindole enantiomer has the following formula:

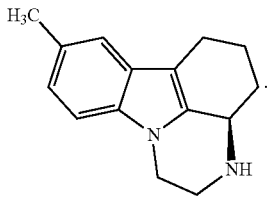

For the purpose of the present invention, (R)-pirlindole enantiomer may, for example, be obtained according to the method described by P. Chiap et al. in "*Automated determination of pirlindole enantiomers in plasma by on-line coupling of a pre-column packed with restricted access material to a chiral liquid chromatographic column*" *Journal of Pharmaceutical and Biomedical Analysis*, 97(2002) 447-455.

According to this method, (R)-pirlindole may be synthesised by derivatisation of racemic pirlindole with R-phenethylisocyanate, separation of the corresponding diastereoisomers by preparative LC, hydrolysis and recrystallization.

The (R)-pirlindole provided in the present invention is enantiomerically pure.

The present invention is based on the findings that (R)-pirlindole enantiomer shows an antagonistic effect on $\alpha_{2A}$ adrenergic receptors.

In modulating of the underlying mechanisms of the symptom of pain, there is a very relevant intervention of adrenergic receptors. These receptors are the targets of catecholamines, especially noradrenaline (norepinephrine) and adrenaline (epinephrine).

There are two large groups of adrenergic receptors, $\alpha$-adrenergic receptors and $\beta$-adrenergic receptors. The $\alpha$-adrenergic receptors are divided in sub-groups $\alpha_1$ and $\alpha_2$. Finally, $\alpha_2$ adrenergic receptors have three subtypes with high genetic homology: adrenergic receptors $\alpha_{2A}$, $\alpha_{2B}$ and $\alpha_{2C}$. These receptors play a critical role in modulating the activity of the neurotransmitters at the level of the sympathetic nervous system and in adrenergic neurons in the central nervous system.

The state of the art contains information which allows asserting that $\alpha_{2A}$ and $\alpha_{2C}$ receptors are involved in the regulation of pre-synaptic neurotransmitter release from sympathetic nerve endings and noradrenergic neurons located in the central nervous system.

$\alpha_{2A}$ adrenergic receptors inhibit neurotransmitter release after high frequency nervous stimulation, while $\alpha_{2C}$ adrenergic receptors modulate neurotransmission in the presence of lower frequencies nerve stimulation.

However, in the central nervous system most of the $\alpha_{2A}$ receptors are located in post-synaptic neurons in relation to noradrenergic endings. These $\alpha_{2A}$ receptors are located in regions of the central nervous system that contribute to the regulation of higher cognitive functions such as the prefrontal cortex.

(R)-pirlindole, as well as all of its pharmaceutically acceptable forms, comprising pharmaceutically acceptable salts of (R)-pirlindole, is a compound that inhibits selectively and reversibly monoamine oxidase type A enzyme.

Additionally, and unexpectedly, the (R)-pirlindole enantiomer shows an antagonistic effect on $\alpha_{2A}$ adrenergic receptors.

The selective antagonist effect of the (R)-pirlindole enantiomer on the $\alpha_{2A}$ adrenergic receptors justifies its use in the treatment of various forms of pain and in the potentiation of the analgesic effect of additional analgesic agents when used in a combination therapy with those agents.

Therefore the subject invention provides (R)-pirlindole enantiomer and its pharmaceutically acceptable salts as an alternative and new agent for the preventive and therapeutic treatment of pain, more specifically, neuropathic pain, including pain associated with any type of peripheral neuropathy.

The inventors of the present application have found that (R)-pirlindole enantiomer or its pharmaceutically acceptable salts may be used alone as the sole active ingredient or as part of a combination therapy with additional analgesic agents in the therapeutic treatment and prevention of pain.

(R)-pirlindole as $\alpha_{2A}$ adrenergic receptor antagonist is associated with an opioid-sparing effect through the potentiating of the analgesic activity of these drugs. The opioid-sparing effect of (R)-pirlindole is associated with a decrease in the incidence rate of side effects like nausea and vomiting, drowsiness, pruritus and urticaria, constipation, respiratory depression, hormone imbalance, confusion, hallucinations, delirium, hypothermia, bradycardia or tachycardia, orthostatic hypotension, dizziness, headache, urinary retention, ureteric or biliary spasm, muscle rigidity, myoclonus, flushing or tolerance. Consequently, (R)-pirlindole will contribute to decrease the risk of mortality, disruption of work and accident-proneness linked with the opioid use.

In fact when (R)-pirlindole enantiomer or its pharmaceutically acceptable salts are used in a combination therapy with additional analgesic agents, the analgesic effect of these additional analgesic agents is potentiated, so that a lower dose of active ingredients is needed to achieve the desirable therapeutic effect thereby reducing the risk of occurrence of adverse reactions, dependence and tolerance to these analgesic drugs.

The coadministration of (R)-pirlindole enantiomer or its pharmaceutically acceptable salts together with at least one additional analgesic agent, allows reducing the dose of the analgesic agents from 25-50% from the dose taken in a non combination therapy.

The coadministration or use in a combination therapy of (R)-pirlindole and additional analgesic agents includes the coadministration of (R)-pirlindole or a pharmaceutically acceptable salt thereof with at least one, (two, three, four, etc.) additional analgesic agents, where the formulation of the active ingredients is either in a fixed-dose (single product) or in separate dose products, where each active ingredient is formulated in a suitable form to be administered in simultaneous or sequential form.

The present invention contemplates the presentation of the said product for combination therapy in a combination pack together with instructions of use.

The additional analgesic agents or drugs contemplated to be used according to the present invention in a combination therapy with (R)-pirlindole or its pharmaceutically acceptable salts, comprise at least one compound or drug from the following list: compounds that decrease neuronal hyperexcitability, such as, inhibitors of the sodium channels (carbamazepine, oxcarbazepine, eslicarbazepine, phenytoin, valproic acid), calcium channel antagonists (pregabalin), ionotropic and metabotropic glutamate receptor antagonists, γ-aminobutyric acid activity enhancers (gabapentin) or μ, κ, and δ opioid receptor agonists, partial agonists/antagonists and antagonists.

Additionally, a patient who suffers from pain or that might suffer from pain in the future, more specifically of neuropathic Pain associated with any type of peripheral neuropathy may benefit from using, according to the present invention, in a fixed or a separate combination therapy, (R)-pirlindole or its pharmaceutically acceptable salts and at least one compound or drug from the following list: compounds with any mechanism of action other than decreasing neuronal hyperexcitability, such as, paracetamol, nonsteroidal anti-inflammatory drugs (acetylsalicylic acid, diclofenac, nabumetone, nimesulide, nabumetone, etodolac, piroxicam, lysine clonixinate, diflunisal, acemetacin, glucametacin, indometacin, proglumetacin, oxametacin, sulindac, aceclofenac, fentiazac, ketorolac, zomepirac, meloxicam, tenoxicam, lornoxican, fenoprofen, fenbufeno, flurbiprofen, benoxaprofen, ibuprofen, ketoprofen, dexetoprofen, pirprofen, indoprofen, naproxen, oxaprozin, tiaprofen, dexibuprofen, meclofenamic acid, mefenamic acid, flufenamic acid, tolfenamic acid, niflumic acid, etofenamate, azapropazone, orgotein, feprazone, morniflumate, tenidap, glycosaminoglycan, polysulfate, celecoxib, rofecoxib, parecoxib, valdecoxib, and etoricoxib), glucosamine or diacerein.

The present invention contempt contemplates the provision of compositions comprising an effective amount of (R)-pirlindole compound or a pharmaceutically acceptable salt thereof which are formulated into pharmaceutical compositions in combination with one or more pharmaceutically acceptable carriers, vehicles or excipients according to known methods for preparing pharmaceutically useful compositions.

Such formulations are described in detail in a number of sources which are well known and readily available to those skilled in the art. For example, Remington's The Science and Practice of Pharmacy, edited by Allen, Loyd V., Jr, 22nd edition, describe the making of formulations which can be used in connection with the subject invention.

Pharmaceutical compositions of the present invention can be formulated to be administered to humans and other mammals orally, (in liquid or solid forms) rectally, parenterally, intracisternally, intravaginally, intraperitoneally, topically (in the form of powders, ointments or drops), buccally or in the form of an oral or nasal spray. The term 'parenterally', as used here, refers to modes of administration, including intravenous, intramuscular, intraperitoneal, intrasternal, subcutaneous, intra-articular injection and infusion.

Pharmaceutical compositions for parenteral injection include aqueous or non-aqueous solutions, dispersions, suspensions or emulsions, pharmaceutically acceptable sterile or non-sterile, and powders for reconstitution in sterile injectable solutions or dispersions.

If it is required, and for a more effective distribution, the compounds of the invention can be embedded in extended controlled release or directed administration systems, such as polymeric matrices, liposomes and microspheres.

The dosage of (R)-pirlindole compound or the pharmaceutically acceptable salt thereof administered to an individual will be dependent upon the response desired and may be dependent upon the subject to be treated, its age, health, weight, frequency of treatment etc. For example, dosage levels contemplated according to the present invention comprise, from 0.1 to 10 mg/kg for oral administration, from 0.01 to 10 mg/kg for intravenous administration.

The (R)-pirlindole molecule has a secondary amine group, which has basic characteristics, thereby easily forming acid salts, which can be, in the context of the present invention, pharmaceutically acceptable acid salts.

Representative pharmaceutically acceptable acid salts include, but are not limited to acetate, adipate, alginate, citrate, aspartate, benzoate, benzenesulfonate, bisulfate, butyrate, camphorate, camphorsulfonate, digluconate, fumarate, glycerophosphate, hemisulfate, heptanoate, hexanoate, fumarate, hydrochloride, hydrobromide, hydrogen iodide, 2-hydroxyethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate, undecanoate and mandelate.

Examples of acids that can be used to form preferred pharmaceutically acceptable acid salts with the (R)-pirlindole compound of the invention, include inorganic acids such as hydrochloric acid, hydrobromic acid, sulfuric acid and phosphoric acid and organic acids, such as methanesulfonic acid, citric acid, mandelic acid, succinic acid and citric acid.

Preferred pharmaceutically acceptable salts are: (R)-pirlindole-(S)mandelate salt, (R)-pirlindole mesylate salt and (R)-pirlindole citrate salt.

The following examples are intended to illustrate the invent on and should not be understood as limiting the scope of the present invention.

EXAMPLES

Example 1

Tablets of R-Pirlindole Hydrochloride

Manufacture of the tablets proceeded by direct compression and included mixing all components, passing them through a sieve and pressing with a suitable compressing force at the required relative atmospheric humidity.

Qualitative and Quantitative composition (amounts are given as weight % of the total composition)

| | |
|---|---|
| (R) - Pirlindole hydrochloride | 25.00 |
| Colloidal Silicon Dioxide | 1.50 |
| Lactose monohydrate | 45.50 |
| HPMC | 2.00 |
| Cellulose microcrystalline | 21.00 |
| Croscarmellose sodium | 4.00 |
| Calcium stearate | 1.00 |

Tablets of R-Pirlindole Hydrochloride

Manufacture of the tablets proceeded by wet granulation followed by compression, including granulating the active ingredient with a suitable solution, drying and passing through a sieve, adding the necessary excipients and pressing with a suitable compression force at the required relative atmospheric humidity.

Qualitative and Quantitative composition (amounts are given as weight % of the total composition)

| | |
|---|---|
| (R) - Pirlindole hydrochloride | 25.00 |
| Cellulose microcrystalline | 15.00 |
| Lactose monohydrate | 50.00 |
| HPMC | 4.00 |
| Croscarmellose sodium | 5.00 |
| Calcium stearate | 1.00 |

Oral Solution of R-Pirlindole Hydrochloride

| | Formula | | Functional |
|---|---|---|---|
| Compounds name | µg/ml | % | Category |
| Active compound: | | | |
| (R) - Pirlindole hydrochloride | 5720 | 100.00 | Active compound |
| Excipients: | | | |
| Purified water | — | — | Solvent agent |

Injectable Solution of R-Pirlindole Hydrochloride

| | Formula | | Functional |
|---|---|---|---|
| Compounds name | µg/ml | % | Category |
| Active compound: | | | |
| (R) - Pirlindole hydrochloride | 5720 | 100.00 | Active compound |
| Excipients: | | | |
| Purified water | — | — | Solvent agent |

The (R)-Pirlindole Hydrochloride oral and injectable solutions were prepared by dissolving the active ingredient in water until complete dissolution.

Example 2

Testing the $\alpha_{2A}$ adrenergic receptor antagonist activity of (R)-pirlindole enantiomer.

The functional $\alpha_{2A}$ adrenergic receptor antagonism assay was carried out in a platform in which the morphological response of CHO (Chinese hamster ovary) cells expressing $\alpha_{2A}$ receptors was assessed. The functional assay was performed using as test items the (R)-pirlindole and the (rac)-pirlindole.

The CHO cells, expressing the human $\alpha_{2A}$ adrenergic receptor were plated the day before the experiment in an adequate culture medium. The compounds were added to the wells and readings were taken 6 minutes later. Responses from the samples were compared to control responses to assess agonist or antagonist activity. The percentage of maximal activity (% Maximum Activity) translates the percentage of agonist activity induced by the $\alpha_{2A}$ agonist, UK-14304 (5-Bromo-N-(2-imidazolin-2-yl)-6-quinoxalin-amine, 5-Bromo-N-(4,5-dihydro-1H-imidazol-2-yl)-6-quinoxalinamine, brimonidine) commercialized by the company Sigma-Aldrich.

(R)-pirlindole enantiomer and (rac)-pirlindole counteracted the agonist activity of UR-14304 on the $\alpha_{2A}$ adrenergic receptor, differently. Unexpectedly, (R)-pirlindole presented $\alpha_{2A}$ receptor antagonist activity. For example, at a concentration of 10 µM, the agonist activity of UK-14304 in the presence of (R)-pirlindole (59.72%) is lower than that presented in the presence of (rac)-pirlindole (89.02%). Accordingly, (R)-pirlindole inhibits agonist activity by 40.28%, whereas (rac)-pirlindole only inhibits agonist activity by 10.98%. Thus, (rac)-pirlindole presented an antagonist activity on $\alpha_{2A}$ adrenergic receptors of about four times (4×) less than (R)-pirlindole.

TABLE 1

Percentage of maximum agonist activity induced by UK-14304

| Concentration | % Maximum Agonist Activity | |
|---|---|---|
| (µM) | (R)-pirlindole | (rac)-pirlindole |
| 10 | 59.72 | 89.02 |
| 5 | 87.37 | 96.50 |
| 1 | 107.76 | 98.47 |

These unexpected results sustain the benefit of (R)-pirlindole for the treatment of pain, specifically the neuropathic pain syndromes.

Lisbon, May 8, 2014.

The invention claimed is:

1. A method for therapeutic treatment of pain, comprising administering orally to a subject in need thereof an effective amount of (R)-pirlindole enantiomer or a pharmaceutically acceptable salt thereof, wherein the pain is neuropathic pain, and the (R)-pirlindole is enantiomerically pure.

2. The method according to claim 1, further comprising administering at least one additional analgesic agent.

3. The method according to claim 2, wherein the at least one additional analgesic agent is administered together with the (R)-pirlindole enantiomer or the pharmaceutically acceptable salt thereof in a single dose form.

4. The method according to claim 2, wherein the at least one additional analgesic agent is administered separately with the (R)-pirlindole enantiomer or the pharmaceutically acceptable salt thereof.

5. The method according to claim 2, wherein the at least one additional analgesic agent is administered simultaneously with the (R)-pirlindole enantiomer or the pharmaceutically acceptable salt thereof.

6. The method according to claim 2, wherein the (R)-pirlindole enantiomer or the pharmaceutically acceptable salt thereof potentiates the effects of the at least one additional analgesic agent in the treatment of pain.

7. The method according to claim 1, wherein the (R)-pirlindole enantiomer or the pharmaceutically acceptable salt thereof is (R)-pirlindole (S)-mandelate salt.

8. The method according to claim 1, wherein the (R)-pirlindole enantiomer or the pharmaceutically acceptable salt thereof is (R)-pirlindole mesylate salt.

9. The method according to claim 1, wherein the (R)-pirlindole enantiomer or the pharmaceutically acceptable salt thereof is (R)-pirlindole citrate salt.

10. The method according to claim 2, wherein the at least one additional analgesic agent is a compound that decrease neuronal hyperexcitability selected from the group consisting of an inhibitor of sodium channels, a calcium channel antagonist, an ionotropic and metabotropic glutamate receptor antagonist, a γ-aminobutyric acid activity enhancers, a μ, κ, and δ opioid receptor agonist, a μ, κ, and δ opioid receptor partial agonists/antagonist, and a μ, κ, and δ opioid receptor antagonist.

11. The method according to claim 10, wherein the inhibitor of sodium channel is selected from the group consisting of carbamazepine, oxcarbazepine, eslicarbazepine, phenytoin, and valproic acid.

12. The method according to claim 10, wherein the calcium channel antagonist is pregabalin.

13. The method according to claim 10, wherein the γ-aminobutyric acid activity enhancer is gabapentin.

14. The method according to claim 2, wherein the at least one additional analgesic agent is a compound selected from the group consisting of paracetamol, nonsteroidal anti-inflammatory drugs, glucosamine and diacerein.

15. The method according to claim 14, wherein the nonsteroidal anti-inflammatory drug is selected from the group consisting of acetylsalicylic acid, diclofenac, nabumetone, nimesulide, etodolac, piroxicam, lysine clonixinate, diflunisal, acemetacin, glucametacin, indometacin, proglumetacin, oxametacin, sulindac, aceclofenac, fentiazac, ketorolac, zomepirac, meloxicam, tenoxicam, lornoxican, fenoprofen, fenbufeno, flurbiprofen, benoxaprofen, ibuprofen, ketoprofen, dexketoprofen, pirprofen, indoprofen, naproxen, oxaprozin, tiaprofen, dexibuprofen, meclofenamic acid, mefenamic acid, flufenamic acid, tolfenamic acid, niflumic acid, etofenamate, azapropazone, orgotein, feprazone, morniflumate, tenidap, glycosaminoglycan, polysulfate, celecoxib, rofecoxib, parecoxib, valdecoxib, and etoricoxib.

16. The method according to claim 1, wherein the (R)-pirlindole enantiomer or the pharmaceutically acceptable salt thereof is administered together with pharmaceutically acceptable carriers, vehicles or excipients.

17. The method according to claim 1, wherein the (R)-pirlindole enantiomer or the pharmaceutically acceptable salt thereof is administered in a dosage of from 0.1 to 10 mg/kg for oral administration.

* * * * *